Nov. 13, 1951 F. SPANBAUER Plant Pat. 1,048
ROSE PLANT
Filed Aug. 31, 1950
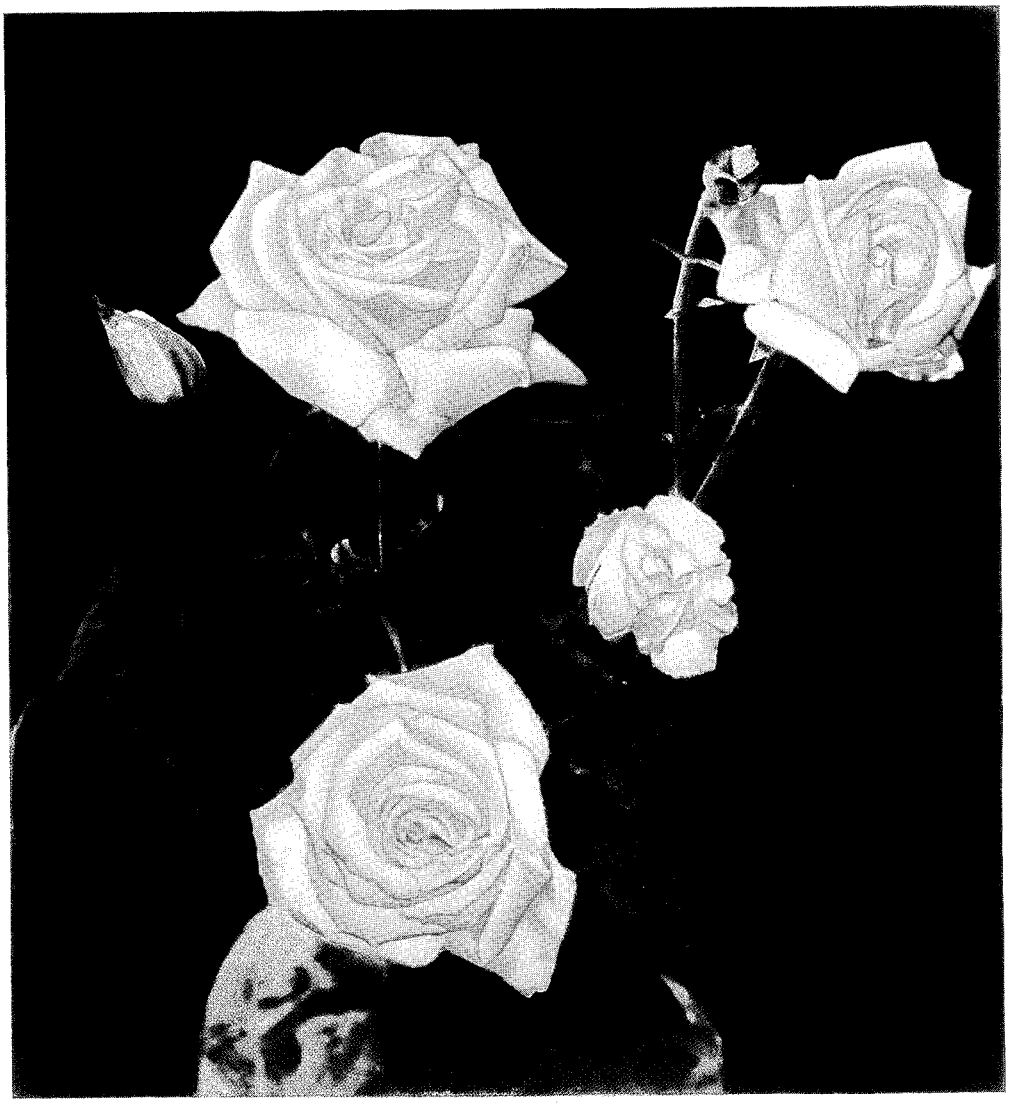
Inventor.
Frank Spanbauer
By: Robb & Robb
Attorneys Patented Nov. 13, 1951 Plant Pat. 1,048

UNITED STATES PATENT OFFICE 1,048

ROSE PLANT

Frank Spanbauer, Decatur, Ill.

Application August 31, 1950, Serial No. 182,548

1 Claim. (Cl. 47—61)

The present invention relates to a new and distinct variety of rose plant of the hybrid tea class, originated by crossing two unnamed and unpatented white seedlings.

As the result of this cross, I have produced a new variety of white rose which is definitely distinct from both parents, as well as from any other variety of which I am aware. About the only similarity of the new variety to any known variety is that the foliage somewhat resembles that of the variety "Ophelia" (unpatented) in respect to the shape and color of the leaves. The blooms, however, are quite different and have many more petals than the blooms of either parent, and the petals have no trace of the usual delicate pink color near the base, as is characteristic of many white roses.

Otherwise, the new variety is more highly resistant to blackspot and mildew than its parents, and is further characterized by its stronger stems and thicker leaves.

Generally speaking, the new variety is dominantly characterized as to novelty by its very double, many-petaled, full-bodied, pure white blooms of superior substance and beauty which are retained over an extended period of time, by the large size and longevity of its blooms, and by its very strong stems and medium large, leathery leaves.

Asexual reproduction of the variety by cuttings, grafting and budding at Decatur, Illinois, shows that the foregoing characteristics come true to form and are established and transmitted through succeeding propagations.

The accompanying drawing shows specimens of the new variety, with the flowers in different stages of development from small bud to full-open bloom.

The following is a detailed description of the new variety, with color terminology in accordance with Ridgway's Color Standards and Nomenclature, except where color terms of ordinary dictionary significance are obvious:

Type: Hardy; greenhouse and outdoor; for cut flowers and garden decoration.
Class: Hybrid tea.
Parentage: Seedling.
*Seed parent.*—An unnamed white seedling.
*Pollen parent.*—An unnamed white seedling.
Propagation: Holds its distinguishing characteristics through succeeding propagations by cuttings, budding, and grafting.

*Flower*

Locality where grown: Decatur, Illinois.
Flowers borne: Singly; regular; on strong, medium length stems.

Quantity of bloom: Free, outdoors, and in greenhouse.
Continuity: Continuous.
Fragrance: Moderate.
Bud:
*Peduncle.*—Long; medium heavy; stiff; Citron-Green, Plate XXXI; entirely smooth.
*Before calyx breaks.*—Size—large. Form—pointed, globular, with conspicuous neck, but without foliaceous appendages. Color—Light Bice-Green, Plate XVII.
*As calyx breaks.*—Color—Pale Yellow-Green, Plate VI.
*As first petal opens.*—Size—medium. Form—globular. Color—outside: very light, Greenish-White; inside: very light, Greenish-White. Opening—opens up well, but slowly, thereby resulting in excellent keeping quality.
Bloom:
*Size.*—Large; 4 to 5 inches.
*Petalage.*—Very double (many petals, usually with no stamens showing); from fifty-five to sixty-five petals arranged regularly.
*Form.*—Flat, cupped; becoming very flat; petals being at first and remaining at maturity very tightly rolled outward.
Petals: Thick; leathery; with inside satiny and outside satiny.
*Shape.*—Outside—oval, with one tip at apex. Intermediate—oval, with one tip at apex. Inside—oval.
*Color at maturity.*—Outside petal—White, Plate LIII. Intermediate petal—White, Plate LIII. Inner petal—White, Plate LIII.
*General color effect.*—White, Plate LIII.
*Behavior.*—Persist; after extended period of time, outer edge turns dark Brown (towards decay).
*Flower longevity.*—On bush in garden, five to eight days in June. Cut roses grown outdoors and kept at livingroom temperatures six days or more in June. Cut roses grown in greenhouse and kept at livingroom temperatures six days or more in February.

*Reproductive organs*

*Stamens.*—Very few; mixed with petaloids.
*Filaments.*—Short; few; most with anthers.
*Color.*—White to Whitish-Green.
*Anthers.*—Large; Reddish-Brown; open at various times.
*Pollen.*—Very sparse (almost none); Yellow.
*Pistils.*—Many.

*Styles.*—Uneven; medium length; medium heavy; bunched.

*Stigma.*—Yellow on tip, but Red part way.

*Ovaries.*—All enclosed in calyx.

*Hips.*—Globular; with Yellow inconspicuous neck; moderately smooth; walls thick and dry.

*Sepals.*—Permanent; moderate length; spear-shaped; curved. Color—Green.

*Seeds.*—Few; medium size.

*Plant*

Foliage:

*Leaves.*—Compound of five leaflets; normal abundance; medium size; heavy; leathery.

*Leaflets.*—Ovoid; base round; margin simply serrate.

*Color.*—Mature — upper surface: Forest Green, Plate XVII; under surface: Light Elm-Green, Plate XVII. Young—upper surface: very small border of deep Indian Purple, Plate XLIV; under surface: same small border of deep Purple Vinaceous, Plate XLIV.

*Rachis (the supporting stem of the compound leaf).* — Heavy. Upper side — smooth; under side—smooth

*Stipules.*—Moderately long; narrow; with very long points turning out at an angle of 45°.

*Disease.*—Resistant to mildew and black-spot.

Growth:

*Habit.*—Bushy; upright.

*Growth.*—Free and vigorous.

*Canes.*—Heavy.

*Main stems.*—Light Bice-Green, Plate XVII. Thorns—few; short; hooked downward; with broad base. Prickles—none. Hairs—none.

*Branches.*—Bright Green. Thorns—few; short; hooked downward; with broad base. Prickles—none. Hairs—none.

*New shoots.* — Bright Grayish - Green. Thorns—very few; short; hooked downward; with broad base. Prickles—none. Hairs—none.

I claim:

A new and distinct variety of rose plant of the hybrid tea class, characterized as to novelty by its very double, many-petaled, full-bodied, pure white blooms of superior substance and beauty which are retained over an extended period of time, by the large size and longevity of its blooms, and by its very strong stems and medium large, leathery leaves, substantially as shown and described.

FRANK SPANBAUER.

No references cited.